United States Patent
Baral

(10) Patent No.: US 11,454,631 B2
(45) Date of Patent: *Sep. 27, 2022

(54) CANCER DETECTION USING BIOPSY DIGITAL IMAGES

(71) Applicant: Jessika Baral, Union City, CA (US)

(72) Inventor: Jessika Baral, Union City, CA (US)

( * ) Notice: Subject to any disclaimer, the term of this patent is extended or adjusted under 35 U.S.C. 154(b) by 249 days.

This patent is subject to a terminal disclaimer.

(21) Appl. No.: 16/561,279

(22) Filed: Sep. 5, 2019

(65) Prior Publication Data

US 2019/0391154 A1    Dec. 26, 2019

Related U.S. Application Data

(63) Continuation of application No. 15/912,584, filed on Mar. 6, 2018, now abandoned.

(51) Int. Cl.
*G01N 33/574*    (2006.01)

(52) U.S. Cl.
CPC . *G01N 33/57496* (2013.01); *G01N 33/57423* (2013.01)

(58) Field of Classification Search
CPC ............... G01N 33/57496; G01N 33/57423
See application file for complete search history.

*Primary Examiner* — Jerry Lin

(57) ABSTRACT

A cancer prediction engine receives a digital image of a tissue biopsy stained for a presence of a biomarker associated with a presence of cancer in the tissue, determines a set of color attribute values of a color space for each pixel of the digital image, classifies, in view of the color attribute values, each pixel of the digital image between a first subset of pixels depicting tissue and a second subset of pixels not depicting tissue, determines whether the digital image depicts cancerous tissue in view of a number of pixels in the second subset of pixels, and responsive to determining that the digital image depicts cancerous tissue, determines a predicted cancer stage for the digital image of the tissue biopsy based at least in part on a color intensity category associated with the color attribute values for each pixel of the first subset of pixels.

20 Claims, 4 Drawing Sheets

CANCER DETECTION USING BIOPSY DIGITAL IMAGES

RELATED APPLICATIONS

This application is a continuation of U.S. patent application Ser. No. 15/912,584, filed Mar. 6, 2018, which is hereby incorporated by reference in its entirety.

TECHNICAL FIELD

The present disclosure is generally related to computer systems, and more particularly, to cancer detection using biopsy digital images in computer systems.

BACKGROUND

Lung cancer is the leading cause of cancer death for both men and women worldwide. Small cell lung cancer (SCLC), also known as oat cell carcinoma, is the most fatal and aggressive subtype of lung cancer. The five-year survival rate for stage 4 SCLC remains a dismal 2% due to the rapid onset of metastasis. Metastasis is the process by which cancer cells migrate from the primary site to secondary sites via blood vessels. There are two overall stages of SCLC: limited stage and extensive stage; extensive stage SCLC is defined by the metastasis of the cancer past the supraclavicular areas in the lung. Doctors separate the two because the treatment plans differ—surgery, radiation therapy, and chemotherapy are preferred for treating limited stage SCLC, whereas chemotherapy alone is preferred for treating extensive stage SCLC. Unfortunately, if the cancer remains undetected and untreated, the average patient survival time is only 2 to 4 months. This prognosis has not advanced in nearly three decades.

BRIEF DESCRIPTION OF THE DRAWINGS

The present disclosure is illustrated by way of example, and not by way of limitation, and can be more fully understood with reference to the following detailed description when considered in connection with the figures in which.

DETAILED DESCRIPTION

Figure 1:
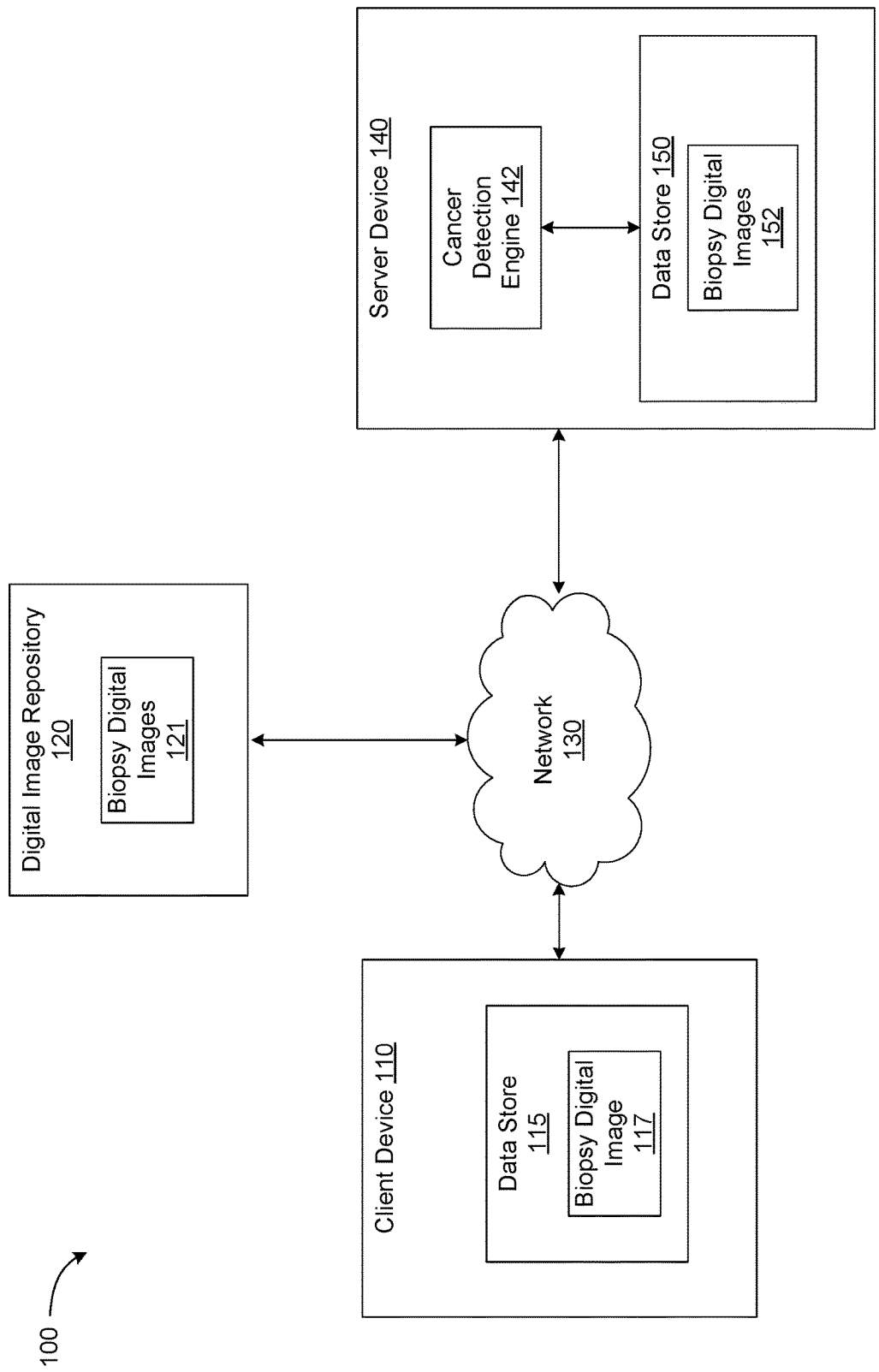
FIG. 1 depicts a high-level component diagram of an example computer system architecture, in accordance with one or more aspects of the present disclosure.

Described herein are methods and systems for cancer detection using biopsy digital images. Due to the excessive costs of screening tests, many cancer patients only go to the doctor only once symptoms begin to show. The stage of cancer cannot be detected until expensive computerized tomography (CT) scans or positron emission tomography (PET) scans (two imaging tests that assess patient health) have been administered to gather further information. Although helpful, CT scans have been shown to be ineffective for SCLC screening purposes. PET scans have proved helpful in predicting the stage of the cancer, but cost thousands of dollars per scan. Currently, a biopsy is taken from the patient's lung and stained with a hematoxylin and eosin (H&E stain). H&E stains are helpful in analyzing tissue biopsies, but are neither cancer-specific nor patient-specific. Light microscopy is used to analyze the stained biopsies. The standard features pathologists look for in stained biopsies include the size, shape, and density of cells. Merkel cell carcinoma is histologically similar to SCLC, making a definitive SCLC diagnosis difficult.

Conventional diagnostic procedures for SCLC are very expensive and can take long periods of time to conduct. Many conventional methods for analyzing biopsies and initiating the correct treatment can often take weeks. SCLC tumors can double in size in as short of a time period as a month, so time is not something that most patients have, and doctors cannot afford to wait weeks before confirming that a patient has extensive stage or limited stage SCLC. While conventional methods for diagnosis are typically thorough, the increases in time and cost present significant obstacles to successfully treating a patient.

Aspects of the present disclosure address the above noted and other deficiencies by implementing a cancer detection engine (e.g., as a computer program or a computer program component) to facilitate cancer detection using biopsy digital images. The cancer detection engine can utilize machine learning models to analyze stored digital images of tissue biopsies that are stained for the presence of a particular biomarker associated with a particular form of cancer. For example, the biopsies can be stained for the presence of Nuclear Factor 1 B, a biomarker that can indicate the presence of SCLC in tissue. The cancer detection engine can analyze the stored digital images to identify color attributes of the pixels within the images and train a machine learning model to separate pixels depicting tissue from pixels not depicting tissue using the color attributes, then use that information to determine whether or not the source images depict cancerous tissue. The cancer detection engine can then train other machine learning models to identify pixels within images of cancerous tissue that are indicative of the presence of the biomarker as well as the color intensity of those pixels, then use that information to make a prediction as to the stage of SCLC in the images. Once the machine learning models are trained against the stored images, the cancer detection engine can receive a new digital image for analysis and use the trained models to assess the received image for the presence of SCLC and if present, predict the stage of cancer present (limited or extensive) based on the digital image.

Aspects of the present disclosure present advantages over conventional solutions to the issues noted above. First, the cancer detection engine of the presence disclosure provides the ability to streamline the diagnostic process for a particular form of cancer by directing analysis based on the concentration of a particular biomarker in a biopsy rather than based on the overall size and shape of the tissue. Additionally, by utilizing multiple machine learning models operating in concert, the cancer detecting engine of the present disclosure can make a cancer detection and stage prediction in minutes rather than weeks. This can significantly improve the efficiency of the diagnostic process by dramatically reducing the time needed to analyze a biopsy for a known form of cancer, which can result in a much shorter timeline necessary to begin a treatment protocol. Moreover, the cancer detection engine of the present disclosure can determine the presence and stage of cancer without the need for expensive scans, which can dramatically reduce the overall costs associated with diagnosis.

FIG. 1 is a block diagram of a network architecture 100 in which implementations of the disclosure may operate. In some implementations, the network architecture 100 can include one or more client devices 110, one or more servers 140, and one or more document repositories 120, which can be in data communication with each other via network 130. Computer system 400 illustrated in FIG. 4 may be one example of any of client devices 110 or servers 140. The network 130 may include, for example, the Internet, intranets, extranets, wide area networks (WANs), local area networks (LANs), wired networks, wireless networks, or other suitable networks, etc., or any combination of two or more such networks. For example, such networks may comprise satellite networks, cable networks, Ethernet networks, and other types of networks.

Client devices 110 may include processor-based systems such as computer systems. Such computer systems may be embodied in the form of desktop computers, laptop computers, personal digital assistants, cellular telephones, smartphones, set-top boxes, music players, web pads, tablet computer systems, game consoles, electronic book readers, or other devices with similar capability. In one embodiment, client device 110 includes a data store 115 that stores one or more biopsy digital images 117 for a user of the client device that are to be analyzed for the presence of disease (e.g., cancer) in the tissue of the biopsy depicted in the digital image.

As noted above, biopsy digital image 117 (as well as biopsy digital images 121, 152) can be a digital image of a biopsy of human tissue that is stained for the presence of a particular biomarker, where the biomarker is associated with the presence of disease in the tissue. For example, digital image 117 can be a digital image of a biopsy of human tissue that is stained with a staining agent of a particular color for the presence of Nuclear Factor 1 B (NFIB) in the cells of the tissue. As noted above, NFIB is a biomarker that can be associated with the presences of small cell lung cancer in the tissue. The presence of the color associated with the staining agent for NFIB in the digital image can be in an indicator of whether or not small cell lung cancer is present in the tissue of the biopsy digital image 117.

In some implementations, biopsy digital image 117 can be received by client device 110 from a scanning device that scans a physical biopsy slide into digital format. Alternatively, the biopsy digital image 117 can be received by the client device from a local connected drive (e.g., flash drive), via a message to the client device (e.g., email, text message, etc.), or the like. Alternatively, biopsy digital image 117 can be retrieved from a digital image repository 120 that stores multiple biopsy digital images 121. Biopsy digital image 117 (as well as biopsy digital images 121 and 152) can be stored in the data store 115 of client device 110 as a tagged image file format (TIFF) image, a Joint Photographic Experts Group (JPEG) image, a JPEG File Interchange Format (JFIF) image, an Exchangeable Image File Format (Exif) image, a Graphics Interchange Format (GIF) image, a Windows bitmap (BMP) image, a Portable Network Graphics (PNG) image, or in any other similar digital image format. In some implementations, biopsy digital image 117 can be an image that has been captured at a particular resolution or magnification. For example, the biopsy digital image 117 can be an image captured at 20 times (20×) magnification by a scanning device.

Biopsy digital image 117 (as well as biopsy digital images 121 and 152) can include multiple pixels. In some implementations, the pixels can be stored using a red-green-blue (RGB) color space model. An RGB color space model is an additive color model in which red, green, and blue are combined to reproduce a variety of different colors. Each pixel of an RGB digital image can include combinations of primary colors or grayscale shades represented by a series of codes. In such instances, a pixel of an RGB digital image can be stored with a code that includes a component for red, a component for green, and a component for blue (e.g. an RGB code). The RGB code can store brightness intensities between 0 and 255 for each of the three color components of the pixel (e.g., 0-255 for red, 0-255 for green, and 0-255 for blue). Accordingly, an RGB value can be stored for a pixel as a three element vector (e.g., (0,0,0)). For example, a black can be represented as (0,0,0), a white pixel can be represented as (255,255,255), a red pixel can be represented as (255,0,0), a green pixel can be represented as (0,255,0), a blue pixel can be represented as (0,0,255), and so on.

In other implementations, other color space models may be used. In one example, the digital image may use a YUV color space model. YUV Images are an affine transformation of the RGB color space, where the Y channel correlates approximately with perceived intensity, while the U and V channels provide color information. In another example, the digital image may use a CMYK color space model. A CMYK image has four channels: cyan, magenta, yellow, and black. CMYK is the standard for print, where subtractive coloring is used. In another example, the digital image may use an HSV color space model. HSV (Hue/Saturation/Value) stores color information in three channels (similar to RGB), but one channel is devoted to brightness (Value), while the other two convey color information. In another example, the digital image may use an HSL (Hue/Saturation/Lightness) color space model. HSL is another alternative representation of an RGB color model that attempts to resemble more perceptual color models such as the Natural Color System (NC S) or Munsell color system, placing fully saturated colors around a circle at a lightness value of ½, where a lightness value of 0 or 1 is fully black or white, respectively. In other implementations, other color space models can be used.

Client device 110 may communicate with one or more digital image repositories 120 that may store biopsy digital images (e.g., biopsy digital images 121). In some implementations, digital image repository 120 may be a local storage system within a local area network. For example, digital image repository 120 may be a file system accessible via a network attached storage (NAS) system, a shared network directory, or the like. In some implementations, digital image repository 120 may be a cloud based document storage system that is accessible to client device 110 via the Internet. Although, for simplicity, only one digital image repository 120 is depicted, in some embodiments, client device 110 may communicate with multiple document repositories 120.

Server device 140 may include, for example, a server computer or any other system providing computing capability. Alternatively, server device 140 may employ a plurality of computing devices that may be arranged, for example, in one or more server banks, computer banks or other arrangements. In some implementations, the computing devices making up server device 140 may be positioned in a single location or may be distributed among many different geographical locations. For example, server device 140 may include a plurality of computing devices that together may comprise a hosted computing resource, a grid computing resource and/or any other distributed computing arrangement.

Server device 140 can include a data store 150 to store biopsy digital images 152. In some implementations, data store 150 can store biopsy digital images 152 in the formats, magnifications, and/or resolutions described above with respect to biopsy digital image 117. In various embodiments, data store 150 can include one or more mass storage devices which can include, for example, flash memory, magnetic or optical disks, or tape drives; read-only memory (ROM); random-access memory (RAM); erasable programmable memory (e.g., EPROM and EEPROM); flash memory; or any other type of storage medium.

Server device 140 can also include cancer detection engine 142. In various implementations, cancer detection engine 142 can receive a biopsy digital image to be analyzed for the presence of cancer (or other disease) in the tissue depicted in the image, and if present, a predicted stage of cancer (or other disease). For example, cancer detection engine 142 can receive a request from client device 110 to analyze biopsy digital image 117 for the presence of cancer in the digital image. In such instances, cancer detection engine 142 can receive the biopsy digital image 117 to be analyzed with the request. Alternatively, cancer detection engine 142 can receive the request with information identifying a biopsy digital image to be analyzed (e.g., a location identifier, file identifier, etc.). For example, the request can include a unique identifier that identifies one of the biopsy digital images 121 stored in digital image repository 120. Similarly, the request can include a unique identifier that identifies one of the biopsy digital images 152 stored in data store 150. Cancer detection engine 142 can then retrieve the identified image and analyze it to determine whether cancer is present in the depicted tissue, and if so, a predicted stage of cancer depicted.

In an illustrative example, cancer detection engine 142 can receive a digital image of a tissue biopsy that is stained for a biomarker (e.g., biopsy digital image 117,121,152), where the biomarker is associated with the presence of cancer (or other disease) in the tissue. Cancer detection engine 142 can analyze the biopsy digital image and determine a set of color properties for each pixel in the received biopsy digital image. In some implementations, cancer detection engine 142 can determine a set of color attribute values of a color space (e.g., RGB color values of an RGB color space) for each pixel in the received biopsy digital image. Once the color attribute values of the color space for each pixel have been determined, cancer detection engine 142 can classify each pixel between a pixel that depicts tissue and a pixel that does not depict tissue based on the color attribute values of the pixel.

Once each pixel in the received biopsy digital image has been classified as tissue or not tissue, cancer detection engine 142 can determine whether the received biopsy digital image depicts cancerous tissue. Cancer detection engine 142 can make this determination based on the number of pixels that are classified as not depicting tissue, since cancerous tissue can often be denser due to cell proliferation in cancerous areas of the tissue. Accordingly, a biopsy digital image with a low number of pixels that do not depict tissue can be indicative of cancerous tissue. If, based on the number of pixels not depicting tissue, cancer detection engine 142 determines that the biopsy digital image does not depict cancerous tissue, a notification can be sent to client device 110 that indicates that that biopsy digital image does not depict cancerous tissue. The client device 110 can then provide the notification for display on a screen, as input to an application program, as a message (e.g., email, text message, alert, etc.), or the like. Similarly, the notification can be provided to server device 140, to be provided as screen output, as input to another application executing on server device 140, as a message, or the like.

If, however, cancer detection engine 142 determines that the biopsy digital image does depict cancerous tissue (based on the number of pixels not depicting tissue), a predicted cancer stage can be determined for the biopsy digital image. Cancer detection engine 142 can make this determination by analyzing the color intensity of the pixels that have been determined as depicting tissue. In some implementations, cancer detection engine 142 can analyze the color attribute values of the color space of each of the pixels in the biopsy digital image that depict tissue, and determine the predicted cancer stage for the tissue based at least in part on the color intensities. The predicted cancer stage for the tissue depicted in the received biopsy digital image can then be provided as output to the server device 140, the client device 110, and application, a screen, a message recipient, etc. as described above.

In various implementations, cancer detection engine 142 can complete the above analyses and determinations using machine learning (ML), artificial intelligence (AI), or recurrent neural network (RNN) models that are trained to perform particular classifications. In such instances, the models can initially be trained using stored biopsy digital images that have been pre-classified. For example, cancer detection engine 142 can conduct the training process for each model by accessing biopsy digital images 121 of digital image repository 120 and/or biopsy digital images 152 of data store 150.

As described above, cancer detection engine 142 may be an application component that executes entirely on server device 140. In other implementations, cancer detection engine 142 may function in whole or in part on client device 110 that communicates with server device 140. In other implementations, cancer detection engine 142 can function as a web-based or cloud-based application that is accessible to a user via a web browser or thin-client user interface that executes on client device 110. In some implementations, a portion of cancer detection engine 142 may execute on client device 110 and another portion of cancer detection engine 142 may execute on server device 140. For example, the digital image to be analyzed for a cancer prediction can be stored and analyzed by the portion of cancer detection engine 142 executed on client device 160, while the training and execution of the various machine learning classifiers may be managed by the portion of cancer detection engine 142 executed by server device 140. Cancer detection engine 142 is described in further detail below with respect to FIG. 2.

Figure 2:
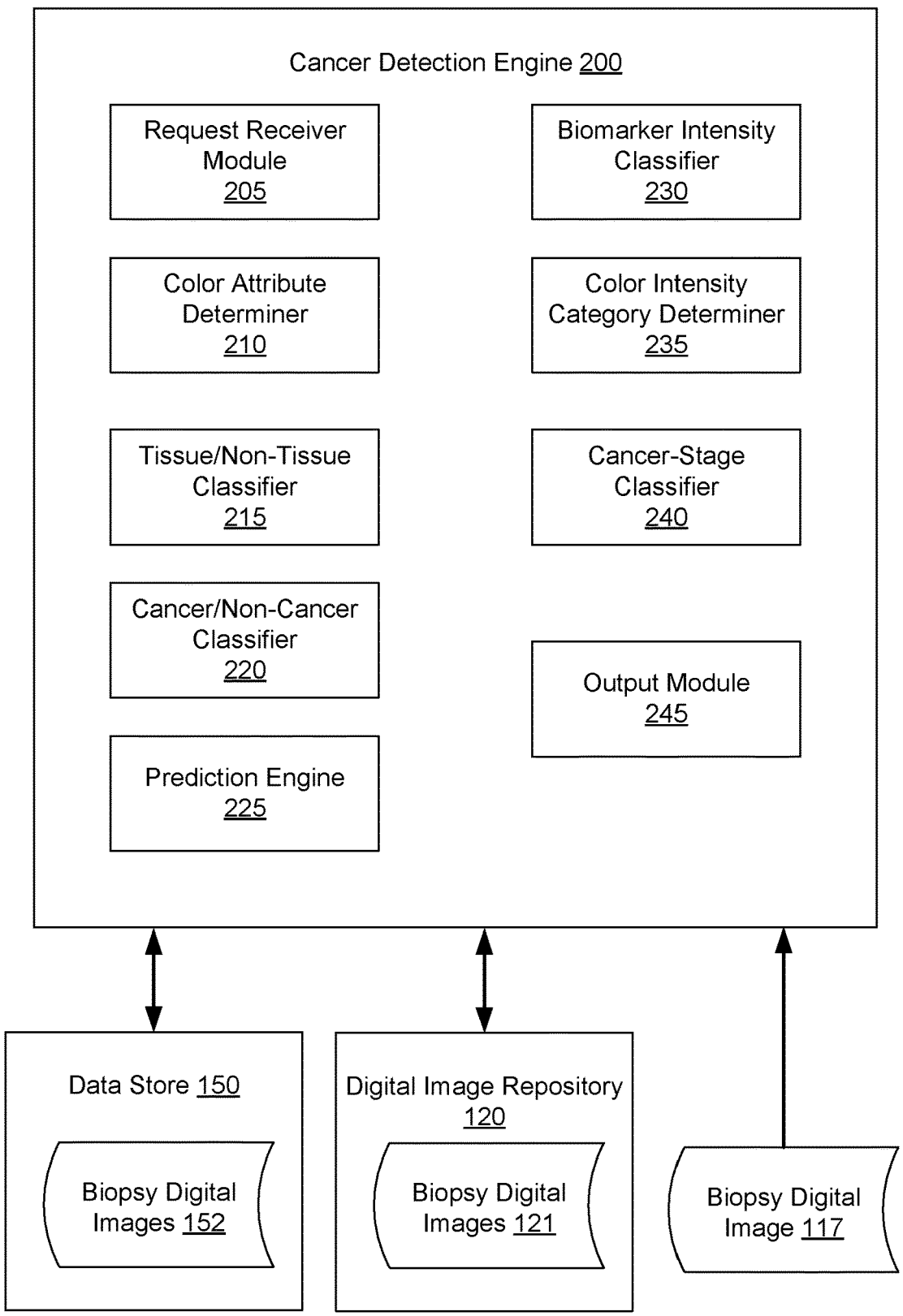
FIG. 2 depicts a block diagram illustrating an example of a cancer detection engine, in accordance with one or more aspects of the present disclosure.

FIG. 2 depicts a block diagram illustrating an example of a cancer detection engine 210 for facilitating cancer detection and cancer stage prediction for biopsy digital images. In some implementations, cancer detection engine 210 may correspond to cancer detection engine 142 of FIG. 1. As shown in FIG. 2, cancer detection engine can include request receiver module 205, color attribute determiner 210, tissue/non-tissue classifier 215, cancer/non-cancer classifier 220, prediction engine 225, biomarker intensity classifier 230, color intensity category determiner 235, cancer-stage classifier 240, and output module 245. Alternatively, the functionality of one or more of request receiver module 205, color attribute determiner 210, tissue/non-tissue classifier 215, cancer/non-cancer classifier 220, prediction engine 225, biomarker intensity classifier 230, color intensity category determiner 235, cancer-stage classifier 240, and output module 245 can be combined into a single module or divided into multiple sub-modules.

Request receiver module 205 is responsible for receiving a digital image of a tissue biopsy stained for the presence of a particular biomarker (biopsy digital image 117). As described above with respect to FIG. 1, request receiver module 205 may receive a request from a client device (e.g., client device 110 of FIG. 1) to analyze the biopsy digital image. The request may include the image itself, or a location and/or unique identifier associated with the biopsy digital image so that request receiver module 205 can retrieve the biopsy digital image for analysis.

In various implementations, the biomarker can be associated with the presence of cancer (or other disease) in the tissue. In one example, the biomarker can be Nuclear Factor 1 B (NFIB) that is associated with the presence of small cell lung cancer in the tissue. In such instances, the biopsy digital image 117 can depict biopsy tissue stained with a staining agent to highlight the presence of NFIB in the tissue. In another example, the biomarker can be microphthalmia-associated transcription factor (MITF) that is associated with the presence of melanoma in the tissue. In another example, the biomarker can be Tripartite Motif Containing 59 (TRIM59) that can be associated with indicating the disease status of early tumorigenesis in tissue. In other implementations, the biomarker can be any type of biomarker where there is a qualitative difference in biomarker staining between the tissues that are healthy and those that are diseased (e.g., cancerous). As such, while the cancer detection engine 200 is described with respect to detecting and predicting the stage of cancer in tissue, in other implementations, aspects of the present disclosure can be applied to the detection and stage prediction of other disease present in tissue where a biomarker can be used to identify the presence of that disease.

Color attribute determiner 210 is responsible for determining a set of color attribute values of a color space (also referred to as "color attribute values" herein) for each pixel of the received biopsy digital image. As described above, the biopsy digital image may be stored with RBG value vectors for each pixel in the image. In other implementations, the biopsy digital image may be stored with color attribute values of other color spaces (e.g., YUV color values of a YUV color space, Cyan-Magenta-Yellow-Black(CMYK) color values of a CMYK color space, Hue-Saturation-Value (HSV) color values of an HSV color space, or Hue-Saturation-Lightness(HSL) color values of an HSL color space). Color attribute determiner 210 can analyze each pixel of the received digital image (e.g., biopsy digital image 117), and determine the color attribute values for each pixel for use by other components of cancer detection engine 200.

Tissue/non-tissue classifier 215 is responsible for classifying each pixel of the received biopsy digital image between a group of pixels depicting tissue and another group of pixels not depicting tissue. As noted above, a determination on whether cancer is present in tissue can be made based on a number of non-tissue pixels present in the image. In some instances, biopsies can include cross sections of tissue where pockets of air are present in the tissue. For example, lung tissue includes air sacs that, when biopsied, can result in areas of the biopsy that do not include tissue. Tissue/non-tissue classifier 215 can examine the pixels in the biopsy digital image and classify each pixel as tissue or non-tissue (e.g., empty space) based on the color attribute values for that pixel.

In some implementations, tissue/non-tissue classifier 215 can generate and execute a machine learning (ML) model, artificial intelligence (AI) model, or recurrent neural network (RNN) model that performs the classification between pixels depicting tissue and pixels not depicting tissue. For example, tissue/non-tissue classifier 215 can generate a logistic regression machine learning model. In other embodiments, tissue/non-tissue classifier 215 can generate and execute another type of ML, AI, or RNN model.

In an illustrative example, tissue/non-tissue classifier 215 can receive sets of digital images that can be used to generate the model. In various implementations, tissue/non-tissue classifier 215 can receive the sets of images from a server data store (e.g., biopsy digital images 152 of data store 150), a network connected digital image repository (e.g., biopsy digital images 121 of digital image repository 120), or the like. Tissue/non-tissue classifier 215 can receive a first group of digital images that each include at least one area of pixels with RGB color values indicative of depicting tissue, and a second group of digital images that each include at least one area of pixels with color attribute values indicative of not depicting tissue. In various embodiments, these groups of digital images may be pre-categorized and classified in order to train the machine learning model used by tissue/non-tissue classifier 215 to classify the pixels of the received biopsy digital image 117.

Tissue/non-tissue classifier 215 can analyze the color attribute values of the two groups of digital images and generate a machine learning model (e.g., a logistic regression machine learning model) that is trained to classify between pixels depicting tissue and pixels not depicting tissue. In an illustrative example, the machine learning model can be generated to identify one or more color attribute values that are indicative of a pixel that depicts empty space within a biopsy digital image (e.g., non-tissue) versus one or more color attribute values that are indicative of a pixel that depicts something other than empty space (e.g., tissue within the biopsy digital image). Once the machine learning model has been trained, tissue/non-tissue classifier 215 can execute the machine learning model to analyze each pixel of biopsy digital image 117 and classify each pixel between pixels depicting tissue and pixels not depicting tissue. Tissue/non-tissue classifier 215 can maintain and store the classification of each pixel in a data store (e.g., memory, disk, etc.) as well as the number of pixels classified into each category for later use by other components of cancer detection engine 200.

Cancer/non-cancer classifier 220 is responsible for determining whether or not the received biopsy digital image (e.g., biopsy digital image 117) depicts cancerous tissue (or another disease in the tissue). In various implementations, cancer/non-cancer classifier 220 can make this determination based on the number of pixels in the biopsy digital image that have been classified as not depicting tissue by tissue/non-tissue classifier 215. As with tissue/non-tissue classifier 215, cancer/non-classifier 220 can generate and execute an ML model, AI model, RNN model, or other similar type of model that performs this classification.

In an illustrative example, cancer/non-cancer classifier 220 can receive sets of digital images that can be used to generate the model. In various implementations, tissue/non-tissue classifier 215 can receive the sets of images from a server data store (e.g., biopsy digital images 152 of data store 150), a network connected digital image repository (e.g., biopsy digital images 121 of digital image repository 120), or the like. In some implementations, cancer/non-cancer classifier 220 can use the same sets of digital images that were used to generate the model used for tissue/non-tissue classifier 215. Alternatively, different sets of digital images can be used.

Cancer/non-cancer classifier 220 can receive a first group of digital images that are each designated as depicting cancerous tissue based on the number of pixels in each image that do not depict tissue. Additionally, cancer/non-cancer classifier 220 can receive a second group of digital images that are each designated as not depicting cancerous tissue based on the number of pixels in each image that do not depict tissue. In various embodiments, these groups of digital images may be pre-categorized and/or classified as depicting cancer or not depicting cancer in order to train the machine learning model used by cancer/non-cancer classifier 220 to classify the received biopsy digital image 117.

Cancer/non-cancer classifier 220 can analyze the numbers of pixels that do not depict tissue for each group of received digital images and generate a machine learning model (e.g., a logistic regression machine learning model) that is trained to classify between digital images depicting cancerous tissue and digital images not depicting cancerous tissue. In an illustrative example, the machine learning model determines a probability of a digital image depicting cancerous tissue based on the number of pixels in the image that do not depict tissue. In an alternative example, the machine learning model can be generated that determines a threshold number of pixels not depicting tissue that can indicate whether a biopsy digital image depicts cancerous tissue and assesses the received biopsy digital image (e.g., biopsy digital image 117) using that threshold number. In such instances, if the received biopsy digital image includes a number of pixels that do not depict tissue (as determined by tissue/non-tissue classifier 215) that is lower than the threshold, then the machine learning model can determine that the received digital image depicts cancerous tissue.

Once the machine learning model has been trained, cancer/non-cancer classifier 220 can execute the machine learning model to determine whether or not the received biopsy digital image depicts cancerous tissue. If cancer/non-cancer classifier 220 determines that the received biopsy digital image does not depict cancerous tissue, output module 245 can be invoked to provide a notification (e.g., to a server device, a client device, an executing application, a message recipient, etc.) indicating that the received biopsy digital image does not depict cancerous tissue. If, however, cancer/non-cancer classifier 220 determines that the received biopsy digital image does depict cancerous tissue, prediction engine 225 can be invoked to predict the stage of cancer (or other disease) present in the tissue.

Prediction engine 225 is responsible for determining a predicted cancer stage (or applicable disease stage) for the received biopsy digital image. In various implementations, prediction engine 225 can make this determination based at least in part on a color intensity category associated with the color attribute values for each pixel in the received biopsy digital image (e.g., biopsy digital image 117) that depicts tissue. In other words, prediction engine 225 can analyze those pixels depicting tissue in the received biopsy digital image, assess the color intensity of those pixels, and make a prediction based at least in part on the assessed color intensities. In some implementations, the prediction can be made additionally based on other information such as the amount of tissue area, the amount of non-tissue area, etc. In various embodiments, prediction engine 225 can make its determination by invoking at least one of biomarker intensity classifier 230, color intensity category determiner 235, and cancer-stage classifier 240.

Biomarker intensity classifier 230 is responsible for classifying each pixel of the received biopsy digital image depicting tissue between a subgroup of pixels depicting the presence of the biomarker and another subgroup of pixels not depicting the presence of the biomarker. As noted above, the staining agent used in staining the biopsy for the biomarker can vary within the image where a darker stain intensity can indicate a more significant presence of the biomarker in the tissue, a lighter stain intensity can indicate a less significant presence or an absence of the biomarker in the tissue. Accordingly, a darker color (e.g., higher/darker color intensity) can indicate a greater concentration of the biomarker in the tissue and a lighter color (e.g., lower/lighter color intensity) can indicate a lower concentration or absence of the biomarker in the tissue. As with tissue/non-tissue classifier 215 and cancer/non-classifier 220, biomarker intensity classifier 230 can generate and execute an ML model, AI model, RNN model, or other similar type of model that performs this classification.

In an illustrative example, biomarker intensity classifier 230 can receive sets of digital images that can be used to generate the model. In various implementations, biomarker intensity classifier 230 can receive the sets of images from a server data store (e.g., biopsy digital images 152 of data store 150), a network connected digital image repository (e.g., biopsy digital images 121 of digital image repository 120), or the like. In some implementations, biomarker intensity classifier 230 can use the same sets of digital images that were used to generate the model used for tissue/non-tissue classifier 215 and cancer/non-cancer classifier 220. Alternatively, different sets of digital images can be used.

Biomarker intensity classifier 230 can receive a first group of digital images that each include at least one area of pixels with color attribute values indicative of depicting the presence of the biomarker in the tissue, and a second group of digital images that each include at least one area of pixels with color attribute values indicative of not depicting the presence of the biomarker in the tissue. In various embodiments, these groups of digital images may be pre-categorized and classified in order to train the machine learning model used by biomarker intensity classifier 230 to classify the pixels of the received biopsy digital image 117.

Biomarker intensity classifier 230 can analyze the color attribute values of the two groups of digital images and generate a machine learning model (e.g., a logistic regression machine learning model) that is trained to classify between pixels depicting the presence of the biomarker and pixels not depicting the presence of the biomarker. In an illustrative example, the machine learning model can be generated to identify one or more color attribute values that are indicative of a pixel depicting a color associated with the presence of the biomarker within a biopsy digital image versus one or more color attribute values that are indicative of a pixel that does not depict the presence of the biomarker. By analyzing the two groups of known images, the model can be generated to identify particular color intensity values and/or ranges of values (e.g., RGB values or RGB value ranges) that are indicative of the presence of the biomarker stain as well as values and/or ranges that are indicative of the absence of the biomarker.

Once the machine learning model has been trained, biomarker intensity classifier 230 can execute the machine learning model to analyze each pixel of biopsy digital image 117 and classify each pixel between pixels depicting the biomarker and pixels not depicting the biomarker. Biomarker intensity classifier 230 can maintain and store the classification of each pixel (biomarker present/biomarker not present) in a data store (e.g., memory, disk, etc.) as well as the number of pixels classified into each category for later use by other components of cancer detection engine 200.

Color intensity category determiner 235 is responsible for determining a color intensity category for each of the pixels analyzed by biomarker intensity classifier 230 (e.g., pixels depicting tissue and the presence of the biomarker and pixels depicting tissue and not depicting the presence of the biomarker). In some implementations, color intensity category determiner 235 can identify a set of color intensity categories, where the set includes a range of RGB color values between a maximum color intensity associated with the presence of the biomarker (e.g., the darkest color associated with the biomarker stain color) and a maximum color intensity associated with the absence of the biomarker (e.g., the color associated with the least amount of biomarker stain color and/or no biomarker stain color).

In some implementations, the range of color attribute values can be a configured with a predetermined number of categories and range delimiters based on historically collected data for biopsy digital images stained for the particular biomarker stain color. For example, a predetermined set of categories can be configured with nine total categories, where the nine categories are divided to span a range of RGB color values from dark blue (maximum presence of the biomarker) to pale blue (maximum absence of the biomarker). In other implementations, other numbers of categories and other RGB color value ranges can be used. Alternatively, the range of RGB values can be determined by the machine learning model generated for biomarker intensity classifier 230. In such cases, when biomarker intensity classifier 230 determines whether a pixel depicts the biomarker, it can also determine the number of categories as well as the range delimiters based on the identified RGB values of the pixels.

Once the number of categories and the range of color attribute values for each category have been determined, color intensity category determiner 235 can then analyze the pixels analyzed by biomarker intensity classifier 230 (e.g., pixels depicting tissue and the presence of the biomarker and pixels depicting tissue and not depicting the presence of the biomarker). Color intensity category determiner 235 can analyze the color attribute values of each pixel and select the color intensity category for that pixel from the set of color intensity categories. In some implementations, color intensity category determiner 235 can maintain and store the color intensity category of each pixel in a data store (e.g., memory, disk, etc.) as well as the number of pixels classified into each color intensity category for later use by cancer-stage classifier 240.

Cancer-stage classifier 240 is responsible for determining the predicted cancer stage (or other disease stage) for the received biopsy digital image (e.g., biopsy digital image 117). In some implementations, cancer-stage classifier 240 can make this determination based at least in part on the color intensity category for each pixel determined by color intensity category determiner 235. In some implementations, cancer-stage classifier 240 can make this determination additionally based on information determined by other components of cancer detection engine 200 such as tissue/non-tissue classifier 215. As with other components of cancer detection engine 200 noted above, cancer-stage classifier 240 can generate and execute an ML model, AI model, RNN model, or other similar type of model that performs the determination of the cancer stage.

In an illustrative example, cancer-stage classifier 240 can receive sets of digital images that can be used to generate the model. In various implementations, cancer-stage classifier 240 can receive the sets of images from a server data store (e.g., biopsy digital images 152 of data store 150), a network connected digital image repository (e.g., biopsy digital images 121 of digital image repository 120), or the like. In some implementations, cancer-stage classifier 240 can use the same sets of digital images that were used to generate the model used for the other classifiers of cancer detection engine 200. Alternatively, different sets of digital images can be used.

Cancer-stage classifier 240 can receive a first group of digital images that are each designated as depicting cancerous tissue for a first stage of cancer, and a second group of digital images that are each designated as depicting cancerous tissue for a second stage of cancer. In an illustrative example, the first group of images can depict cancerous tissue for a "limited stage" of small cell lung cancer (e.g., non-metastasized cancer) and the second group of images can depict cancerous tissue for an "extensive stage" of small cell lung cancer (e.g., cancer that has spread to other tissues in the body). In various embodiments, these groups of digital images may be pre-categorized and/or classified as depicting a first stage of cancer or a second stage of cancer in order to train the machine learning model used by cancer-stage classifier 240 to determine the predicted cancer stage for received biopsy digital image 117.

Cancer-stage classifier 240 can then determine an image characteristic set for each of the images in the two groups. In some implementations, the image characteristic set can be determined by utilizing the other components of cancer detection engine 200. In one illustrative example, the image characteristic set can be determined by determining the number of pixels not depicting tissue (e.g., determined by tissue/non-tissue classifier 215), determining the number of pixels depicting the presence of the biomarker (e.g., determined by biomarker intensity classifier 230), the number of pixels not depicting the presence of the biomarker (e.g., determined by biomarker intensity classifier 230), and the number of pixels in each of the color intensity categories (e.g., determined by color intensity category determiner 235). For example, color intensity category determiner 235 identified nine total color intensity categories to be used, cancer-stage classifier 240 would utilize the total number of pixels for each of the nine color intensity categories.

Cancer-stage classifier 240 can then analyze the image characteristic sets for the two groups of images and generate a model that is trained to classify between digital images depicting cancerous tissue at the first cancer stage (e.g., limited small cell lung cancer) and digital images depicting cancerous tissue at the second cancer stage (e.g., extensive small cell lung cancer). In an illustrative example, cancer-stage classifier 240 can generate a multinomial machine learning model to make this classification. Once the multinomial machine learning model has been trained, cancer-stage classifier 240 can execute the model to classify the received biopsy digital image between an image depicting the first cancer stage and an image depicting the second cancer stage. Once the cancer stage prediction has been made, output module 245 can be invoked to provide the predicted stage as output.

Output module 245 is responsible for providing output notifications that indicate whether or not a received biopsy digital image depicts cancerous tissue, and if so, the predicted stage of cancer depicted. In various implementations, output module 245 can provide a notification to a client device or a server device. The notification may then be provided for display on a screen or other display device, as input to an application program, as a message (e.g., email, text message, alert), or the like.

As noted above, while the components of cancer detection engine 200 have been described as detecting a particular biomarker (e.g., NFIB) for particular stages (e.g., limited and extensive) of a particular disease (e.g., small cell lung cancer), aspects of the present disclosure can be implemented in a similar fashion for the detection of other stages of other tissue diseases that can be identified by the presence of other biomarkers.

Figure 3:
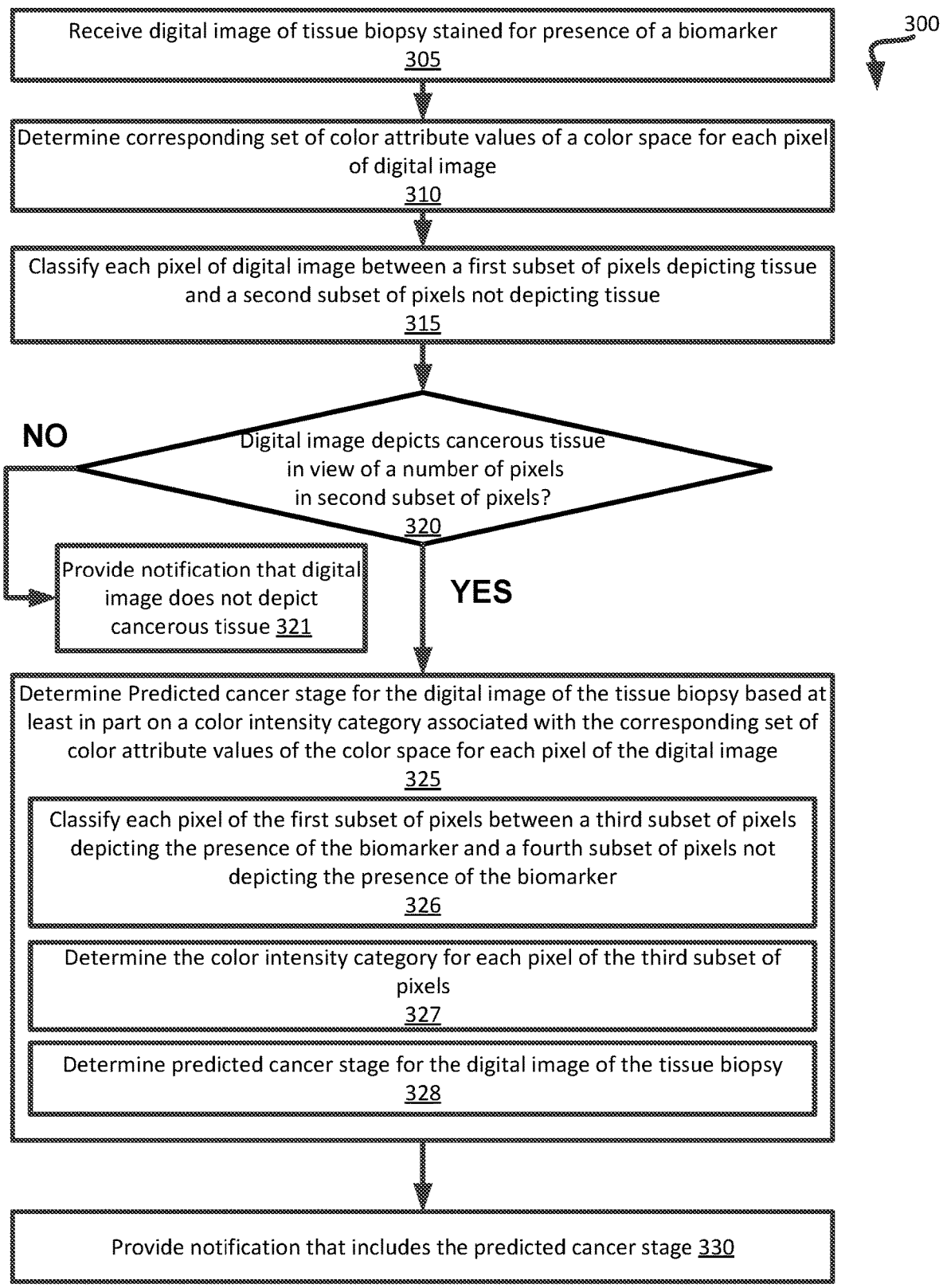
FIG. 3 depicts a flow diagram of a method for cancer detection using biopsy digital images, in accordance with one or more aspects of the present disclosure.

FIG. 3 depicts a flow diagram of an example method 300 for cancer detection using biopsy digital images. The method may be performed by processing logic that may comprise hardware (circuitry, dedicated logic, etc.), computer readable instructions (run on a general purpose computer system or a dedicated machine), or a combination of both. In an illustrative example, method 300 may be performed by cancer detection engine 142 in FIG. 1, or cancer detection engine 200 in FIG. 2. Alternatively, some or all of method 300 might be performed by another module or machine. It should be noted that blocks depicted in FIG. 3 could be performed simultaneously or in a different order than that depicted.

At block 305, processing logic receives a digital image of a tissue biopsy stained for the presence of a biomarker. In some implementations, the biomarker is associated with the presence of cancer in the tissue, and the digital image includes multiple pixels. At block 310, processing logic determines a set of color attribute values of a color space for each pixel in the digital image received at block 305. In some implementations, the color attribute values can include at least one of Red-Green-Blue (RGB) color values of an RGB color space, YUV color values of a YUV color space, Cyan-Magenta-Yellow-Black (CMYK) color values of a CMYK color space, Hue-Saturation-Value (HSV) color values of an HSV color space, or Hue-Saturation-Lightness (HSL) color values of an HSL color space. At block 315, processing logic classifies, in view of the color attribute values of the color space determined at block 310, each pixel in the digital image between a first subset of pixels depicting tissue and a second subset of pixels not depicting tissue.

At block 320, processing logic determines whether the digital image depicts cancerous tissue in view of a number of pixels in the second subset of pixels. If not, processing proceeds to block 321 where processing logic provides a notification that the digital image does not depict cancerous tissue. Otherwise, processing continues to block 325. At block 325, processing logic determines a predicted cancer stage for the digital image of the tissue biopsy based at least in part on a color intensity category associated with the set of color attribute values of the color space for each pixel of the first subset of pixels. In some implementations, processing logic can make this determination by invoking blocks 326, 327, and 328.

At block 326, processing logic classifies, in view of the color attribute values of the color space determined at block 310, each pixel of the first subset of between a third subset of pixels depicting the presence of the biomarker and a fourth subset of pixels not depicting the presence of the biomarker. At block 327, processing logic determines, in view of the color attribute values of the color space determined at block 310, the color intensity category for each pixel of the third subset of pixels and the fourth subset of pixels. At block 328, processing logic determines the predicted cancer stage for the digital image of the tissue biopsy based at least in part on the color intensity category for each pixel of the third subset of pixels and the fourth subset of pixels.

At block 330, processing logic provides a notification that includes the predicted cancer stage. The notification can be provided to client device, a server device, an application, a message recipient, or the like.

Figure 4:
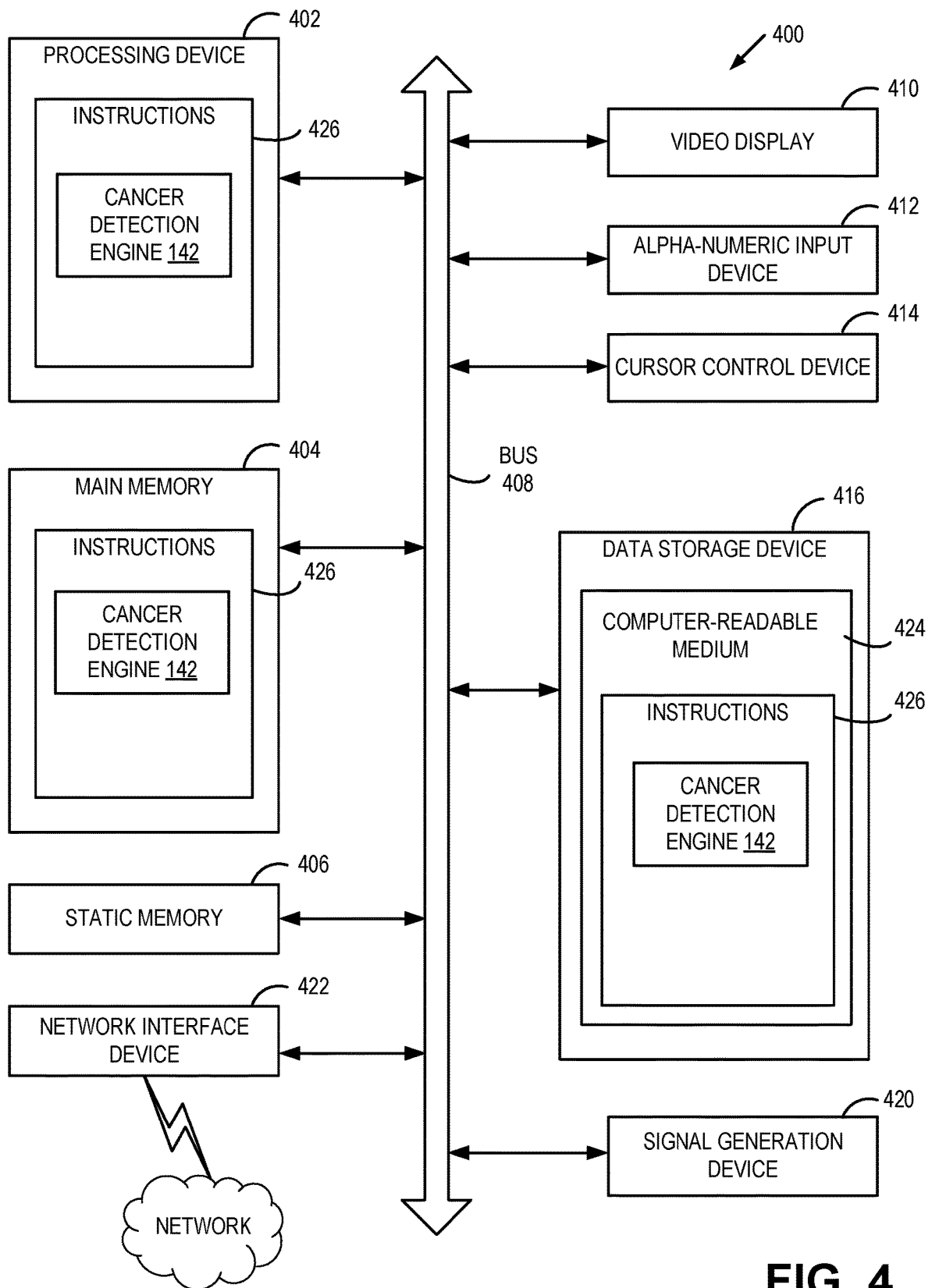
FIG. 4 depicts a block diagram of an illustrative computer system operating in accordance with one or more aspects of the present disclosure.

FIG. 4 depicts an example computer system 400 which can perform any one or more of the methods described herein. In one example, computer system 400 may correspond to computer system 100 of FIG. 1. The computer system may be connected (e.g., networked) to other computer systems in a LAN, an intranet, an extranet, or the Internet. The computer system may operate in the capacity of a server in a client-server network environment. The computer system may be a personal computer (PC), a set-top box (STB), a server, a network router, switch or bridge, or any device capable of executing a set of instructions (sequential or otherwise) that specify actions to be taken by that device. Further, while a single computer system is illustrated, the term "computer" shall also be taken to include any collection of computers that individually or jointly execute a set (or multiple sets) of instructions to perform any one or more of the methods discussed herein.

The exemplary computer system 400 includes a processing device 402, a main memory 404 (e.g., read-only memory (ROM), flash memory, dynamic random access memory (DRAM) such as synchronous DRAM (SDRAM)), a static memory 406 (e.g., flash memory, static random access memory (SRAM)), and a data storage device 416, which communicate with each other via a bus 408.

Processing device 402 represents one or more general-purpose processing devices such as a microprocessor, central processing unit, or the like. More particularly, the processing device 402 may be a complex instruction set computing (CISC) microprocessor, reduced instruction set computing (RISC) microprocessor, very long instruction word (VLIW) microprocessor, or a processor implementing other instruction sets or processors implementing a combination of instruction sets. The processing device 402 may also be one or more special-purpose processing devices such as an application specific integrated circuit (ASIC), a field programmable gate array (FPGA), a digital signal processor (DSP), network processor, or the like. The processing device 402 is configured to execute processing logic (e.g., instructions 426) that includes cancer detection engine 142 for performing the operations and steps discussed herein (e.g., corresponding to the method of FIG. 3, etc.).

The computer system 400 may further include a network interface device 422. The computer system 400 also may include a video display unit 410 (e.g., a liquid crystal display (LCD) or a cathode ray tube (CRT)), an alphanumeric input device 412 (e.g., a keyboard), a cursor control device 414 (e.g., a mouse), and a signal generation device 420 (e.g., a speaker). In one illustrative example, the video display unit 410, the alphanumeric input device 412, and the cursor control device 414 may be combined into a single component or device (e.g., an LCD touch screen).

The data storage device 416 may include a non-transitory computer-readable medium 424 on which may store instructions 426 that include cancer detection engine 142 (e.g., corresponding to the method of FIG. 3, etc.) embodying any one or more of the methodologies or functions described herein. Cancer detection engine 142 may also reside, completely or at least partially, within the main memory 404 and/or within the processing device 402 during execution thereof by the computer system 400, the main memory 404 and the processing device 402 also constituting computer-readable media. Cancer detection engine 142 may further be transmitted or received over a network via the network interface device 422.

While the computer-readable storage medium 424 is shown in the illustrative examples to be a single medium, the term "computer-readable storage medium" should be taken to include a single medium or multiple media (e.g., a centralized or distributed database, and/or associated caches and servers) that store the one or more sets of instructions. The term "computer-readable storage medium" shall also be taken to include any medium that is capable of storing, encoding or carrying a set of instructions for execution by the machine and that cause the machine to perform any one or more of the methodologies of the present disclosure. The term "computer-readable storage medium" shall accordingly be taken to include, but not be limited to, solid-state memories, optical media, and magnetic media.

Although the operations of the methods herein are shown and described in a particular order, the order of the operations of each method may be altered so that certain operations may be performed in an inverse order or so that certain operation may be performed, at least in part, concurrently with other operations. In certain implementations, instructions or sub-operations of distinct operations may be in an intermittent and/or alternating manner.

It is to be understood that the above description is intended to be illustrative, and not restrictive. Many other implementations will be apparent to those of skill in the art upon reading and understanding the above description. The scope of the disclosure should, therefore, be determined with reference to the appended claims, along with the full scope of equivalents to which such claims are entitled.

In the above description, numerous details are set forth. It will be apparent, however, to one skilled in the art, that aspects of the present disclosure may be practiced without these specific details. In some instances, well-known structures and devices are shown in block diagram form, rather than in detail, in order to avoid obscuring the present disclosure.

Unless specifically stated otherwise, as apparent from the following discussion, it is appreciated that throughout the description, discussions utilizing terms such as "receiving," "determining," "classifying," "providing," or the like, refer to the action and processes of a computer system, or similar electronic computing device, that manipulates and transforms data represented as physical (electronic) quantities within the computer system's registers and memories into other data similarly represented as physical quantities within the computer system memories or registers or other such information storage, transmission or display devices.

The present disclosure also relates to an apparatus for performing the operations herein. This apparatus may be specially constructed for the specific purposes, or it may comprise a general purpose computer selectively activated or reconfigured by a computer program stored in the computer. Such a computer program may be stored in a computer readable storage medium, such as, but not limited to, any type of disk including floppy disks, optical disks, CD-ROMs, and magnetic-optical disks, read-only memories (ROMs), random access memories (RAMs), EPROMs, EEPROMs, magnetic or optical cards, or any type of media suitable for storing electronic instructions, each coupled to a computer system bus.

Aspects of the disclosure presented herein are not inherently related to any particular computer or other apparatus. Various general purpose systems may be used with programs in accordance with the teachings herein, or it may prove convenient to construct more specialized apparatus to perform the specified method steps. The structure for a variety of these systems will appear as set forth in the description below. In addition, aspects of the present disclosure are not described with reference to any particular programming language. It will be appreciated that a variety of programming languages may be used to implement the teachings of the disclosure as described herein.

Aspects of the present disclosure may be provided as a computer program product that may include a machine-readable medium having stored thereon instructions, which may be used to program a computer system (or other electronic devices) to perform a process according to the present disclosure. A machine-readable medium includes any mechanism for storing or transmitting information in a form readable by a machine (e.g., a computer). For example, a machine-readable (e.g., computer-readable) medium includes a machine (e.g., a computer) readable storage medium (e.g., read only memory ("ROM"), random access memory ("RAM"), magnetic disk storage media, optical storage media, flash memory devices, etc.).

The words "example" or "exemplary" are used herein to mean serving as an example, instance, or illustration. Any aspect or design described herein as "example" or "exemplary" is not to be construed as preferred or advantageous over other aspects or designs. Rather, use of the words "example" or "exemplary" is intended to present concepts in a concrete fashion. As used in this application, the term "or" is intended to mean an inclusive "or" rather than an exclusive "or". That is, unless specified otherwise, or clear from context, "X includes A or B" is intended to mean any of the natural inclusive permutations. That is, if X includes A; X includes B; or X includes both A and B, then "X includes A or B" is satisfied under any of the foregoing instances. In addition, the articles "a" and "an" as used in this application and the appended claims should generally be construed to mean "one or more" unless specified otherwise or clear from context to be directed to a singular form. Moreover, use of the term "an embodiment" or "one embodiment" or "an implementation" or "one implementation" throughout is not intended to mean the same embodiment or implementation unless described as such. Furthermore, the terms "first," "second," "third," "fourth," etc. as used herein are meant as labels to distinguish among different elements and may not have an ordinal meaning according to their numerical designation.

What is claimed is:

1. A method comprising:
receiving, by a processing device, a digital image of a tissue biopsy stained for a presence of a biomarker, wherein the biomarker is associated with a presence of cancer in the tissue, and wherein the digital image comprises a plurality of pixels;
determining a corresponding set of color attribute values of a color space for each pixel of the plurality of pixels;
classifying, in view of the corresponding set of the color attribute values of the color space, each pixel of the plurality of pixels between a first subset of pixels depicting tissue and a second subset of pixels not depicting tissue using a first trained machine learning model;
determining whether the digital image depicts cancerous tissue in view of a number of pixels in the second subset of pixels; and
responsive to determining that the digital image depicts cancerous tissue in view of the number of pixels in the second subset of pixels, determining, by the processing device, a predicted cancer stage for the digital image of the tissue biopsy based at least in part on a color intensity category associated with the corresponding set of color attribute values of the color space for each pixel of the first subset of pixels.

2. The method of claim 1, wherein determining the predicted cancer stage further comprises:
classifying, in view of the corresponding set of color attribute values of the color space, each pixel of the first subset of pixels between a third subset of pixels depicting the presence of the biomarker and a fourth subset of pixels not depicting the presence of the biomarker;
determining, in view of the corresponding set of color attribute values of the color space, the color intensity category for each pixel of the third subset of pixels and the fourth subset of pixels; and
determining the predicted cancer stage for the digital image of the tissue biopsy based at least in part on the color intensity category for each pixel of the third subset of pixels and the fourth subset of pixels.

3. The method of claim 1, wherein classifying each pixel of the plurality of pixels between the first subset of pixels depicting tissue and the second subset of pixels not depicting tissue further comprises:
receiving a first set of digital images, wherein each digital image of the first set of digital images comprises at least one area of pixels with color attribute values of the color space indicative of depicting tissue;
receiving a second set of digital images, wherein each digital image of the second set of digital images comprises at least one area of pixels with color attribute values of the color space indicative of not depicting tissue;
generating, using the first set of digital images and the second set of digital images, the first trained machine learning model, wherein the first trained machine learning model is a logistic regression machine learning model trained to classify between pixels depicting tissue and pixels not depicting tissue; and
executing the logistic regression machine learning model trained to classify between pixels depicting tissue and pixels not depicting tissue.

4. The method of claim 1, wherein determining whether the digital image depicts cancerous tissue further comprises:
receiving a first set of digital images, wherein each digital image of the first set of digital images is designated as depicting cancerous tissue in view of a corresponding amount of pixels not depicting tissue;
receiving a second set of digital images, wherein each digital image of the second set of digital images is designated as not depicting cancerous tissue in view of a corresponding amount of pixels not depicting tissue;
generating, using the first set of digital images and the second set of digital images, a second trained machine learning model, wherein the second trained machine learning model is a logistic regression machine learning model trained to classify between digital images depicting cancerous tissue and digital images not depicting cancerous tissue; and
executing the logistic regression machine learning model trained to classify between digital images depicting cancerous tissue and digital images not depicting cancerous tissue.

5. The method of claim 2, wherein classifying each pixel of the first subset of pixels between a third subset of pixels depicting the presence of the biomarker and a fourth subset of pixels not depicting the presence of the biomarker further comprises:
receiving a first set of digital images, wherein each digital image of the first set of digital images comprises at least one area of pixels with color attribute values of the color space indicative of depicting the presence of the biomarker;
receiving a second set of digital images, wherein each digital image of the second set of digital images comprises at least one area of pixels with color attribute values of the color space indicative of not depicting the presence of the biomarker;
generating, using the first set of digital images and the second set of digital images, a second trained machine learning model, wherein the second trained machine learning model is a logistic regression machine learning model trained to classify between pixels depicting the presence of the biomarker and pixels not depicting the presence of the biomarker; and
executing the logistic regression machine learning model trained to classify between pixels depicting the presence of the biomarker and pixels not depicting the presence of the biomarker.

6. The method of claim 2, wherein determining the color intensity category further comprises:
identifying a set of color intensity categories, wherein the set comprises a range of color attribute values of the color space between a maximum color intensity associated with the presence of the biomarker to a maximum color intensity associated with the absence of the biomarker; and
selecting the color intensity category from the set of color intensity categories in view of the set of color attribute values of the color space for each pixel of the third subset of pixels and the fourth subset of pixels.

7. The method of claim 2, wherein determining the predicted cancer stage for the digital image further comprises:
receiving a first set of digital images, wherein each digital image of the first set of digital images is designated as depicting cancerous tissue for a first stage of cancer;
receiving a second set of digital images, wherein each digital image of the second set of digital images is designated as depicting cancerous tissue for a second stage of cancer;
determining an image characteristic set for each of the first set of digital images and the second set of digital images;
generating, using the image characteristic set for each of the first set of digital images and the second set of digital images, a second trained machine learning model, wherein the second trained machine learning model is a multinomial model machine learning model trained to classify between digital images depicting cancerous tissue at a first cancer stage and digital images depicting cancerous tissue at a second cancer stage; and
executing the multinomial model machine learning model trained to classify between digital images depicting cancerous tissue at the first cancer stage and digital images depicting cancerous tissue at the second cancer stage.

8. The method of claim 1, wherein the color attribute values of the color space comprises at least one of Red-Green-Blue(RGB) color values of an RGB color space, YUV color values of a YUV color space, Cyan-Magenta- Yellow-Black(CMYK) color values of a CMYK color space, Hue-Saturation-Value (HSV) color values of an HSV color space, or Hue-Saturation-Lightness(HSL) color values of an HSL color space.

9. The method of claim 7, wherein the biomarker comprises Nuclear Factor 1 B (NFIB), and the cancer comprises small cell lung cancer, and wherein the first cancer stage comprises a limited stage of small cell lung cancer and the second cancer stage comprises an extensive stage of small cell lung cancer.

10. A computing apparatus comprising:
a memory; and
a processing device, operatively coupled to the memory, to:
receive a digital image of a tissue biopsy stained for a presence of a biomarker, wherein the biomarker is associated with a presence of cancer in the tissue, and wherein the digital image comprises a plurality of pixels;
determine a corresponding set of color attribute values of a color space for each pixel of the plurality of pixels;
classify, in view of the corresponding set of color attribute values of the color space, each pixel of the plurality of pixels between a first subset of pixels depicting tissue and a second subset of pixels not depicting tissue using a first trained machine learning model;
determine whether the digital image depicts cancerous tissue in view of a number of pixels in the second subset of pixels; and
responsive to determining that the digital image depicts cancerous tissue in view of the number of pixels in the second subset of pixels, determine a predicted cancer stage for the digital image of the tissue biopsy based at least in part on a color intensity category associated with the corresponding set of color attribute values of the color space for each pixel of the first subset of pixels.

11. The computing apparatus of claim 10, wherein to determine the predicted cancer stage, the processing device is further to:
classify, in view of the corresponding set of color attribute values of the color space, each pixel of the first subset of pixels between a third subset of pixels depicting the presence of the biomarker and a fourth subset of pixels not depicting the presence of the biomarker;
determine, in view of the corresponding set of color attribute values of the color space, the color intensity category for each pixel of the third subset of pixels and the fourth subset of pixels; and
determine the predicted cancer stage for the digital image of the tissue biopsy based at least in part on the color intensity category for each pixel of the third subset of pixels and the fourth subset of pixels.

12. The computing apparatus of claim 10, wherein to classify each pixel of the plurality of pixels between the first subset of pixels depicting tissue and the second subset of pixels not depicting tissue, the processing device is further to:
receive a first set of digital images, wherein each digital image of the first set of digital images comprises at least one area of pixels with color attribute values of the color space indicative of depicting tissue;
receive a second set of digital images, wherein each digital image of the second set of digital images comprises at least one area of pixels with color attribute values of the color space indicative of not depicting tissue;
generate, using the first set of digital images and the second set of digital images, the first trained machine learning model, wherein the first trained machine learning model is a logistic regression machine learning model trained to classify between pixels depicting tissue and pixels not depicting tissue; and
execute the logistic regression machine learning model trained to classify between pixels depicting tissue and pixels not depicting tissue.

13. The computing apparatus of claim 10, wherein to determine whether the digital image depicts cancerous tissue, the processing device is further to:
receive a first set of digital images, wherein each digital image of the first set of digital images is designated as depicting cancerous tissue in view of a corresponding amount of pixels not depicting tissue;
receive a second set of digital images, wherein each digital image of the second set of digital images is designated as not depicting cancerous tissue in view of a corresponding amount of pixels not depicting tissue;
generate, using the first set of digital images and the second set of digital images, a second trained machine learning model, wherein the second trained machine learning model is a logistic regression machine learning model trained to classify between digital images depicting cancerous tissue and digital images not depicting cancerous tissue; and
execute the logistic regression machine learning model trained to classify between digital images depicting cancerous tissue and digital images not depicting cancerous tissue.

14. The computing apparatus of claim 11, wherein to classify each pixel of the first subset of pixels between a third subset of pixels depicting the presence of the biomarker and a fourth subset of pixels not depicting the presence of the biomarker, the processing device is further to:
receive a first set of digital images, wherein each digital image of the first set of digital images comprises at least one area of pixels with color attribute values of the color space indicative of depicting the presence of the biomarker;
receive a second set of digital images, wherein each digital image of the second set of digital images comprises at least one area of pixels with color attribute values of the color space indicative of not depicting the presence of the biomarker;
generate, using the first set of digital images and the second set of digital images, a second trained machine learning model, wherein the second trained machine learning model is a logistic regression machine learning model trained to classify between pixels depicting the presence of the biomarker and pixels not depicting the presence of the biomarker; and
execute the logistic regression machine learning model trained to classify between pixels depicting the presence of the biomarker and pixels not depicting the presence of the biomarker.

15. The computing apparatus of claim 11, wherein to determine the color intensity category, the processing device is further to:
identify a set of color intensity categories, wherein the set comprises a range of color attribute values of the color space between a maximum color intensity associated with the presence of the biomarker to a maximum color intensity associated with the absence of the biomarker; and select the color intensity category from the set of color intensity categories in view of the set of RGB color values for each pixel of the third subset of pixels and the fourth subset of pixels.

16. The computing apparatus of claim 11, wherein to determine the predicted cancer stage for the digital image, the processing device is further to:

receive a first set of digital images, wherein each digital image of the first set of digital images is designated as depicting cancerous tissue for a first stage of cancer;

receive a second set of digital images, wherein each digital image of the second set of digital images is designated as depicting cancerous tissue for a second stage of cancer;

determine an image characteristic set for each of the first set of digital images and the second set of digital images;

generate, using the image characteristic set for each of the first set of digital images and the second set of digital images, a second trained machine learning model, wherein the second trained machine learning model is a multinomial model machine learning model trained to classify between digital images depicting cancerous tissue at a first cancer stage and digital images depicting cancerous tissue at a second cancer stage; and execute the multinomial model machine learning model trained to classify between digital images depicting cancerous tissue at the first cancer stage and digital images depicting cancerous tissue at the second cancer stage.

17. The computing apparatus of claim 10, the color attribute values of the color space comprises at least one of Red-Green-Blue(RGB) color values of an RGB color space, YUV color values of a YUV color space, Cyan-Magenta-Yellow-Black(CMYK) color values of a CMYK color space, Hue-Saturation-Value (HSV) color values of an HSV color space, or Hue-Saturation-Lightness(HSL) color values of an HSL color space.

18. The computing apparatus of claim 16, wherein the biomarker comprises Nuclear Factor 1 B (NFIB), and the cancer comprises small cell lung cancer, and wherein the first cancer stage comprises a limited stage of small cell lung cancer and the second cancer stage comprises an extensive stage of small cell lung cancer.

19. A non-transitory computer readable storage medium, having instructions stored therein, which when executed by a processing device of a computer system, cause the processing device to:

receive a digital image of a tissue biopsy stained for a presence of a biomarker, wherein the biomarker is associated with a presence of cancer in the tissue, and wherein the digital image comprises a plurality of pixels;

determine a corresponding set of color attribute values of a color space for each pixel of the plurality of pixels;

classify, in view of the corresponding set of color attribute values of the color space, each pixel of the plurality of pixels between a first subset of pixels depicting tissue and a second subset of pixels not depicting tissue using a first trained machine learning model;

determine whether the digital image depicts cancerous tissue in view of a number of pixels in the second subset of pixels; and responsive to determining that the digital image depicts cancerous tissue in view of the number of pixels in the second subset of pixels, determine a predicted cancer stage for the digital image of the tissue biopsy based at least in part on a color intensity category associated with the corresponding set of color attribute values of the color space for each pixel of the first subset of pixels.

20. The non-transitory computer readable storage medium of claim 19, wherein to determine the predicted cancer stage the processing device is further to:

classify, in view of the corresponding set of color attribute values of the color space, each pixel of the first subset of pixels between a third subset of pixels depicting the presence of the biomarker and a fourth subset of pixels not depicting the presence of the biomarker using a second trained machine learning model;

determine, in view of the corresponding set of color attribute values of the color space, the color intensity category for each pixel of the third subset of pixels and the fourth subset of pixels; and determine the predicted cancer stage for the digital image of the tissue biopsy based at least in part on the color intensity category for each pixel of the third subset of pixels and the fourth subset of pixels.

* * * * *